(12) United States Patent
Caldeira

(10) Patent No.: US 6,234,019 B1
(45) Date of Patent: May 22, 2001

(54) SYSTEM AND METHOD FOR DETERMINING A DENSITY OF A FLUID

(75) Inventor: Gilmar M. Caldeira, Sertaozinho (BR)

(73) Assignee: Smar Research Corporation, Ronkonkoma, NY (US)

( * ) Notice: Subject to any disclaimer, the term of this patent is extended or adjusted under 35 U.S.C. 154(b) by 0 days.

(21) Appl. No.: 09/253,830

(22) Filed: Feb. 19, 1999

(51) Int. Cl.[7] .................................................. G01N 9/26
(52) U.S. Cl. .............................................. 73/438; 73/32 R
(58) Field of Search .......................... 73/437, 439, 32 R, 73/434; 702/137, 138

(56) References Cited

U.S. PATENT DOCUMENTS

| | | | |
|---|---|---|---|
| 4,625,553 | * 12/1986 | Charter | 73/438 |
| 5,309,764 | * 5/1994 | Waldrop et al. | 73/302 |
| 5,587,527 | * 12/1996 | Radford et al. | 73/439 |
| 5,591,922 | * 1/1997 | Segeral et al. | 73/861.04 |
| 5,604,315 | * 2/1997 | Briefer et al. | 73/861.49 |
| 5,827,963 | * 10/1998 | Selegatto et al. | 73/438 |
| 5,827,977 | * 10/1998 | Ortiz et al. | 73/861.42 |

* cited by examiner

Primary Examiner—Helen Kwok
(74) Attorney, Agent, or Firm—Kenyon & Kenyon

(57) ABSTRACT

A system and method for obtaining a fluid density of a fluid in a tank includes, for example, a first sensor coupled to a second sensor through an extension. The two sensors are coupled to a transmitter. The sensors are lowered into the fluid of the tank such that the first sensor is positioned at a first fluid level and the second sensor is positioned at a second fluid level. Fluid pressure at the two levels is sensed by the two sensors which affects the fluid pressure of a fill fluid inside the housing of the system. The effect on the fluid pressure of the fill fluid is sensed by the transmitter which creates an electrical signal relating to the fluid pressures sensed by the two sensors. A calculating device may determine the fluid density of the fluid in the tank from the signal received from the transmitter.

44 Claims, 7 Drawing Sheets

SYSTEM AND METHOD FOR DETERMINING A DENSITY OF A FLUID

FIELD OF THE INVENTION

The present invention relates to a system and a method for determining a density of a fluid, and in particular, for measuring density of the fluid in a tank.

BACKGROUND INFORMATION

Obtaining a measurement of a density of a fluid has numerous advantages for various applications. One such application includes, for example, a fermentation of beer. Obtaining density measurements of beer is beneficial in that an indicator for determining whether the beer is properly fermented, i.e., the "Degree Plateau" value, is directly proportional to the density of beer. Obtaining a precise Degree Plateau value is an important indication for obtaining the most favorable results when fermenting beer (or other consumable fluids).

Typically, to measure the density of beer in a beer tank, a beer sample is removed from the beer tank and delivered to a testing facility, where the density of the beer sample is measured. Even though such density measurements may be precise at the time measurements are performed, a transport and a measurement of the sample takes a predetermined amount of time. Therefore, the actual Degree Plateau value of the beer in the tank may not be the most current or the most precise value. Accordingly, the best brewing results may not be achieved using this conventional density measurement method. Another exemplary application in which the determination of the density of the fluid is pasteurization and sterilization of milk.

Other conventional methods and systems for measuring the density in the fluid have also been implemented. One such method provides an assembly having a density sensor and a transmitter. The assembly also includes two tubes which are attached to an external portion of a tank at different fluid levels. The pressure of the fluid in the tank is measured at each fluid level by the pressure sensor, and a pressure signal indicative of the pressure at the particular measured level may be transmitted by the transmitter to a calculating unit. With this method, it may be possible to differentiate between the pressures at the different fluid levels to obtain a density of the fluid. However, this method may provide erroneous readings and measurements depending upon the environmental conditions which may affect the assembly, as well as the pressure sensor and the transmitter. Effectively, the environmental effects (e.g., temperature effects due to sunlight) may effect the measurements of the fluid pressure and the calculations of the density of the fluid. Furthermore, because the sensor/transmitter is externally connected to the tank, the tank must be emptied to access sensor/transmitter parts for scheduled maintenance or cleaning.

Another method for measuring a density in a fluid is described in U.S. Pat. No. 5,211,678. This conventional method provides a reel for lowering a single probe on an electrical cable into a container which maintains the fluid therein. A measurement is taken at the surface of the fluid (in the container), and then at another depth to determine a density of the fluid. However, by using the method described in U.S. Pat. No. 5,211,678, it is possible to obtain inaccurate determination of the density of the fluid because the electrical cable (which is wrapped around a reel) may not be necessarily lowered to predetermined depth levels in the tank. This imprecise procedure of lowering the probe may reduce the precision of the determination of the density of the fluid because an accurate distance between the surface level of the fluid and the predetermined depth levels, thus causing errors in the determination of the fluid density. Furthermore, because of the inaccurate manner in which the reel raises and lowers the cable, it would not be possible to attain reliably consistent density determinations over a number of similar measurements. In addition, this conventional density measurement method provides a delay as the electrical cable is deployed and measurements are taken over several depth levels because only a single probe is utilized. This delay may be substantial over several measurements. Such compounded delays may be unacceptable when an accurate and quick determination of the fluid density is required.

U.S. Pat. No. 4,625,553 describes another conventional system for measuring a density of a drilling mud in an open top tank. This conventional system includes a pair of serially connected pressure sensors internally mounted to inside walls of the tank in the fluid. A constant volume air flow source is connected to an inlet of one pressure sensor, a second pressure sensor is connected to an outlet of the first pressure sensor, and a vent is connected between the second pressure sensor outlet and an external air pressure. A first transducer measures a gas pressure from the air flow source, and a second transducer measures the differential pressure between two pressure sensors. However, when the pressure measurements are taken by these sensors, these measurements may be inaccurate, especially over multiple measurement cycles because the air flow source forcing air throughout the entire system is externally situated, and thus may be subject to varying environmental effects. These environmental effects may cause unreliable measurements and determinations of, for example, pressures and densities of the fluid. Furthermore, because the sensors are mounted to the inside walls of the tank, when it is necessary to perform routine maintenance and cleaning of the tank, the entire tank must be emptied which is inefficient and costly.

SUMMARY OF THE INVENTION

The present invention provides an exemplary embodiment of a system for determining a density of a particular fluid in a tank. The system includes a housing having a first substantially static fluid and a second substantially static fluid, a first sensor coupled to the housing and a second sensor coupled to the housing. The first sensor is disposed in the tank at a first fluid level of the particular fluid, and detects a first fluid pressure at the first fluid level by acting on the first substantially static fluid. The second sensor is disposed in the tank at a second fluid level of the particular fluid, and detects a second fluid pressure at the second fluid level by acting on the second substantially static fluid. The second sensor is positioned at a predetermined distance from the first sensor. The system also includes a transmitter which communicates with the first sensor via the first substantially static fluid and with the second sensor via the second substantially static fluid. The transmitter generates at least one signal corresponding to the density of the particular fluid as a function of the first fluid pressure and the second fluid pressure.

The present invention also provides another embodiment of the system for determining the density of the particular fluid in a tank. This system includes a housing; a first sensor coupled to the housing via a first extension; and a second sensor coupled to the housing via a second extension. The first sensor is positioned at a first fluid level of the particular fluid and senses a fluid pressure at the first fluid level by providing a first substantially static fluid through the first extension. The second sensor is positioned at a second fluid level of the particular fluid and senses the fluid pressure at the second fluid level by providing a second substantially static fluid through the second extension. The second fluid level is different from the first fluid level. This system also includes a transmitter which is provided in the housing. The transmitter is in fluid communication with the first sensor via the first substantially static fluid in the first extension, and in fluid communication with the second sensor via the second substantially static fluid in the second extension. The transmitter generates at least one signal which relates to the fluid pressures sensed by the first sensor at the first fluid level and by the second sensor at the second fluid level.

The present invention also provides an exemplary embodiment of a sensor for determining the pressure of the particular fluid. The sensor includes a sensor housing having a substantially static fluid; and at least two diaphragms which are provided in the sensor housing. Each of the at least two diaphragms act on the substantially static fluid in response to the pressure by the particular fluid.

The present invention also provides another embodiment of a sensor for determining the pressure of the particular fluid. The sensor includes a sensor housing in an approximately spherical shape which encloses a substantially static fluid; and at least one diaphragm which is coupled to the sensor housing. The diaphragm substantially encloses the sensor housing and acts on the substantially static fluid in response to the pressure provided by the particular fluid.

The present invention also provides a method for determining the density of the particular fluid in the tank. In this method, a first sensor is provided in the tank at a first fluid level in the particular fluid, and a second sensor is provided in the tank at a second fluid level in the particular fluid. The second fluid level is different from the first fluid level. A first fluid pressure is sensed at the first fluid level using the first sensor to act on a first substantially static fluid. The first sensor communicates with a transmitter via the first substantially static fluid. A second fluid pressure is sensed at the second fluid level using the second sensor to act on a second substantially static fluid. The second sensor communicates with the transmitter through the second substantially static fluid, and generates at least one signal which relates to the first fluid pressure and the second fluid pressure to determine the density of the particular fluid.

The present invention further provides a method for measuring a fluid pressure of the fluid. In this method, a sensor is provided in the fluid at a particular fluid level. The sensor includes a sensor housing, at least two diaphragms, and a substantially static fluid. The diaphragms are coupled to the sensor housing and are affected by the fluid pressure of the fluid at the particular fluid level. The diaphragms act on the substantially static fluid; and determine the fluid pressure of the fluid at the particular fluid level by measuring displacement of the substantially static fluid.

BRIEF DESCRIPTION OF THE DRAWINGS

FIG. 4 illustrates a second embodiment of the sensor shown in FIG. 2a.

DETAILED DESCRIPTION

Figure 1:
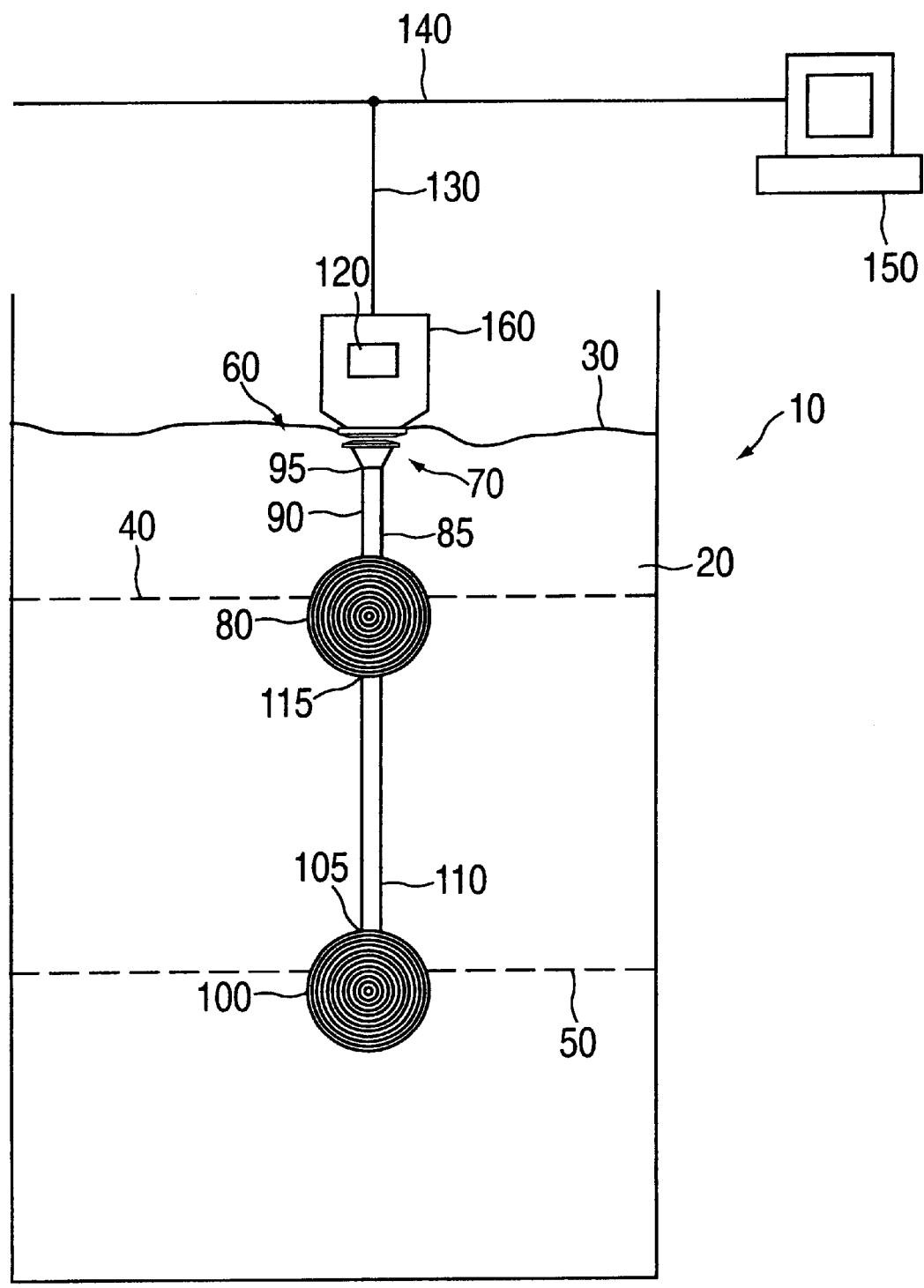
FIG. 1 illustrates an embodiment of a system for measuring a fluid density according to the present invention.

FIG. 1 illustrates a first embodiment of a system 60 according to the present invention for accurately measuring a density of a fluid. A tank 10 facilitates a fluid 20 (e.g., a substantially static fluid) having a surface fluid level 30. The tank 10 may be an open tank (i.e., open to external environmental conditions) or a closed tank (i.e., covered by a cover).

The system 60 includes, e.g., a housing 70, a first sensor 80, a first extension 90, a second sensor 100, a second extension 110, a transmitter 120, a first data bus 130, a second data bus 140 and a computer 150. The housing 70 may include the first extension 90 and the second extension 110. The first sensor 80, the second sensor 100 and/or the transmitter 120 may be provided in the housing 70 or may be externally coupled to the housing 70. The first and second extensions 90, 110 may have a cylindrical shape. Other shapes for the first and second extensions 90, 110 are also possible. The second sensor 100 is coupled to a first end 105 of the second extension 110. The second extension 110, at its second end 115, is coupled to the first sensor 80. The first sensor 80 is coupled to a first end 85 of the first extension 90. The first extension 90, at its second end 95, is coupled to a container portion 160 of the housing 70. The transmitter 120 may be either coupled to the container portion 160 or disposed within the container portion 160.

The elements of the system 60 may be coupled to each other as described above or in other numerous ways. In one embodiment of the system 60 shown in FIG. 1, the first and second sensors 80, 100, the first and second extensions 90, 110 and the container portion 160 can be interconnected via a welding procedure, pressure sealed mating procedure, etc. It is also possible to interconnect these elements by a pressure-sealed interconnection of flanges using sealing rings and/or gaskets therebetween. In addition, the elements of the system 60 can be arranged as a single integral unit.

The structures interconnected as described above may be composed of various substances and materials. In one embodiment of the present invention, the housing 70 is composed of, for example, a plated carbon steel material, a 316 SST material or a Hastelloy C276 material. The sensors 80, 100 may be composed of, for example, a 316L SST material, a Hastelloy C276 material, a Monel 400 material, a tantalum material or a titanium material. The sealing rings or gaskets that are provided in the system may be composed of, for example, at least one of Buna N, Viton or teflon. These materials are provided by, e.g., the Smar International Corporation.

The transmitter 120 is provided in the container portion 160 of the housing 70 and is coupled, e.g., to the first data bus 130 (e.g., a high speed bus, a Fieldbus, etc.). The first data bus 130 is coupled to the second data bus 140 (e.g., a high speed bus, a Fieldbus, etc.). The second data bus 140 is then coupled to the computer 150. It is also possible for a plurality of data buses 130 communicating with a plurality of tanks to be coupled to the second data bus 140. Furthermore, the transmitter 120 may communicate with the computer 150 via a single bus. The transmitter 120 can also communicate with the computer 150 via wireless communication such as, for example, via RF communication, digital communication, etc.

The housing 70 facilitates a static fluid therein. This static fluid can be provided in tubes (not shown in FIG. 1) which are situated in the housing. In an exemplary embodiment according to the present invention, the first and second sensors 80, 100 communicate with the transmitter 120 via the static fluid which is facilitated in the housing 70. For example, the first sensor 80 acts on a first fill fluid of the static fluid via a first tube (not shown in FIG. 1), and the second sensor 100 communicates with a second fill fluid of the static fluid via a second tube (also not shown in FIG. 1).

In use, the housing 70 is lowered into the fluid 20 such that both sensors 80, 100 are below the surface fluid level 30. Thus, the first sensor 80 is disposed at a first fluid level 40 of the fluid 20, and the second sensor 100 is disposed at a second fluid level 50 of the fluid 20. The distance between the first and second sensors 80, 100, and thus between the first and second fluid levels 40, 50, is held substantially constant because the second extension 110 coupled between the first and second sensors 80, 100. For example, the second fluid level 50 is provided below the first fluid level 40 which is below the surface fluid level 30.

The second sensor 100 senses the fluid pressure at the second fluid level 50. The pressure sensed by the second sensor 100 affects the second fill fluid within the second tube by displacing the second fill fluid based on the pressure sensed by the second sensor 100. The displacement of the second fill fluid is sensed and analyzed by the transmitter 120. Similarly, the first sensor 80 senses the fluid pressure at the first fluid level 40. The pressure sensed by the first sensor 80 affects the first fill fluid within the first tube by displacing the first fill fluid based on the pressure sensed by the first sensor 80. The displacement of the first fill fluid is also sensed and analyzed by the transmitter 120.

The transmitter 120 sends a signal, e.g., an electrical signal or a wireless signal, to the computer 150 via the first data bus 130 and via the second data bus 140. The computer 150 can store the signal as data in its storage device. The signal contains information regarding, among other things, a difference between the fluid pressure at the first fluid level 40 and the fluid pressure at the second fluid level 50. The pressures at different fluid levels is based on the displacement of the first and second fill fluids. With this pressure information and the predetermined distance between the two fluid levels 40, 50, the computer 150 can determine the density of the fluid 20.

Other information can also be provided by the signal, e.g., a temperature of the fluid which can be transmitted by a temperature sensor coupled to a housing or situated within a housing. The system can also include at least one temperature sensor. If two sensors are utilized, one temperature sensor may be provided at the first fluid level 40 and another temperature sensor may be provided at the second fluid level 50.

In another preferred embodiment, instead of two fill fluids, only one fill fluid is provided within a single tube, which may be affected by both of the first and second sensors 80, 100. The fill fluid to be used depends on, e.g., the measurements to be taken. These measurements are affected by the sensitivity of the measurements and the composition of the fluid 20. The fill fluid may be composed of a DC-200/20 silicone oil, an MO-10 fluorolube oil, a DC-704 silicone oil, a DC-200/350 food-grade silicon oil and a Neobee M20 propylene glycol oil.

In another embodiment according to the present invention, the first sensor 80 and the second sensor 100 have substantially the same characteristics. For example, each sensor is affected in substantially the same manner by internal and external temperature variations. Such characteristics matching of the sensors enhances the system performance by eliminating erroneous density determinations by possible external variations (e.g., temperature changes) that may occur during the pressure measurements. Accordingly, the fluid density value is virtually free from the environmental effects and the manufacturing defects that may cause erroneous fluid density calculations.

As indicated above, one possible application of the system according to the present invention is for measuring the density of beer in a beer tank to obtain a density/concentration value. Because the housing 70 is located inside the tank 10 and at least partially submerged in the fluid 20, measurements are not substantially affected by external environmental variations. Even a small variation in density that may be caused by the environmental variations (e.g., 5%–6%) may generate a large change in the density/concentration value. However, because the first and second sensors 80, 100 according to the present invention are substantially matched and because the distance between the first sensor 80 and the second sensor 100 is constant, virtually error free density/concentration values may be obtained. Furthermore, because the housing 70 may be easily lowered or raised into the tank 10, the tank need not be emptied to perform a routine maintenance or a cleaning of the housing 70, thus reducing costs and efficiently utilizing the tank 10 and the system 60.

Figure 2A:
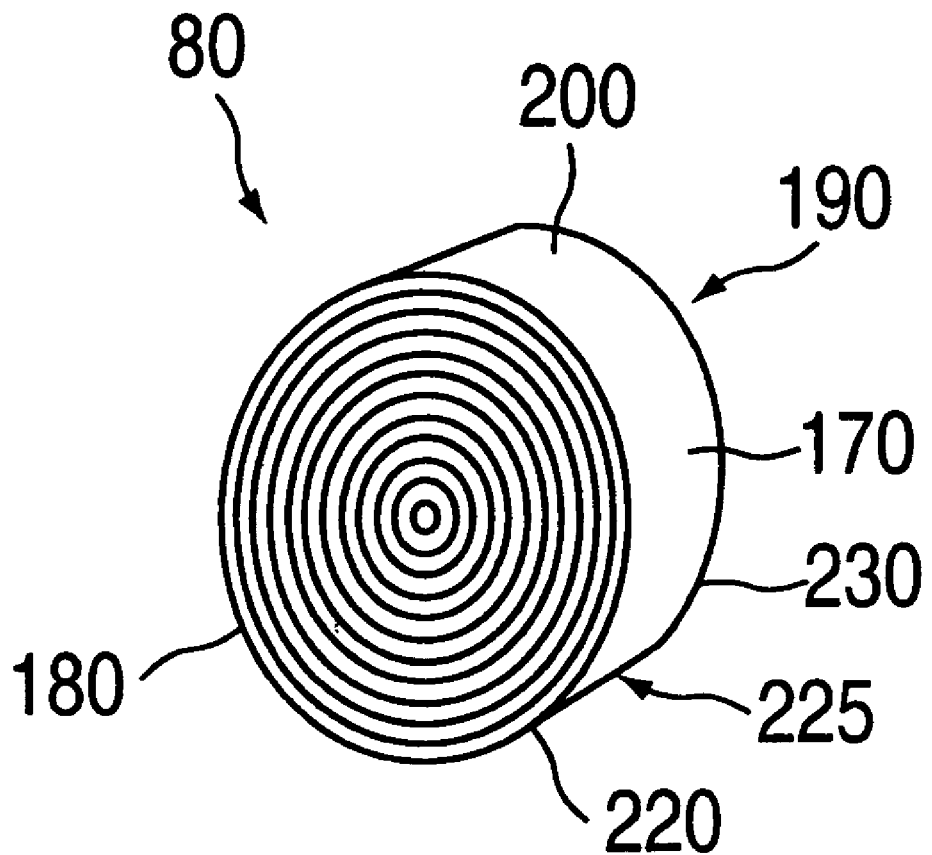
FIG. 2a illustrates a sensor to be used with the system shown in FIG. 1.

FIG. 2a illustrates an exemplary structure of the first sensor 80 according to one embodiment of the present invention. In this embodiment, the first sensor 80 may have the same structure as that of the second sensor 100. The first sensor 80 includes a sensor housing 170, a first diaphragm 180, a second diaphragm 190 (not shown in detail) and a portion 200 for connecting the first sensor 80 to a tube of the first extension 110 of the housing 70. The first diaphragm 180 is provided at a first circular edge 225 of the sensor housing 170 to form a first sensor housing side. The second diaphragm 150 is provided at a second circular edge 230 (not shown in detail) of the housing 170 to form a second sensor housing side. Each of the first and second diaphragms 180, 190 has a flexible surface including flexible parts 220. The sensor housing 170 encloses the portion 200 which communicates with the tube. The portion 200 has a hole which exits the sensor 80 through a side of the sensor housing 170. The sensor 80 is coupled to the housing 70 to allow the portion 200 in the sensor 80 to be coupled to the tube of the first extension 110. Because the sensor housing 170 has the fill fluid therein, this fill fluid communicates with the fill fluid in the housing 70 through the portion 200.

Figure 2B:
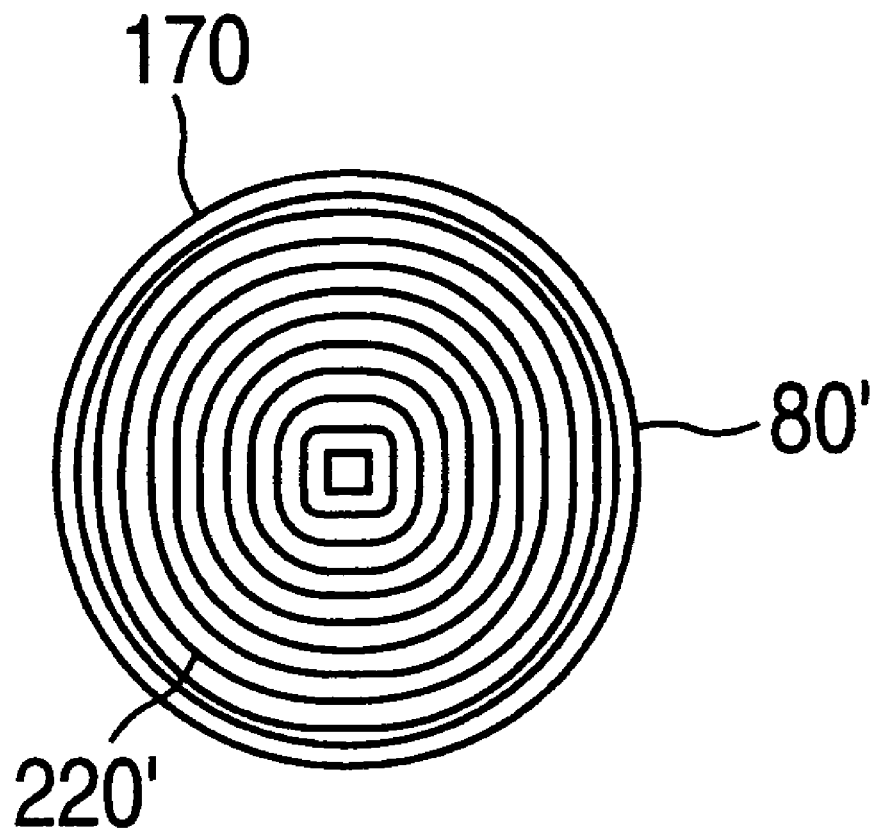
FIG. 2b illustrates another embodiment of the sensor having substantially rounded square concentric regions.

In the embodiment of the first sensor 80 shown in FIG. 2a, the flexible parts 220 have approximately circular concentric regions. The flexible parts 220 may also have other shapes. These shapes may include, for example, approximately rounded regular concentric polygonal regions, rounded square concentric regions (as shown in FIG. 2b), rounded pentagonal concentric regions, rounded hexagonal concentric regions, rounded octagonal concentric regions, etc. for a flexible part 220' of a sensor 80'.

In operation, when the first sensor 80 is lowered into the fluid 20 to the first fluid level 40, the fluid pressure of the fluid 20 at the first fluid level 40 is applied to the first diaphragm 180 and to the second diaphragm 190. The flexible parts 220 of each of the first and second diaphragms 180, 190 are forced inward (e.g., toward a center of the sensor housing 170) in response to the fluid pressure of the fluid 20 at the fluid level 40. The movement of the flexible parts 220 of each of the first and second diaphragms 180, 190 affects the pressure of the fill fluid inside the sensor housing 170. The displacement of the fill fluid in the sensor housing 170 relates to the fluid pressure of the fluid 20 at the first fluid level 40 is provided by the fill fluid inside the portion 200 of the sensor housing 170 through the tube in the first extension 110 of the housing 70 to reach the transmitter 120. The transmitter 120 generates an electrical signal in response to the change in fill fluid pressure.

It may be preferable to use the first and second diaphragms 180, 190 as opposed to using only one diaphragm. To achieve the same sensitivity with only one diaphragm as compared to using two diaphragms would require a much larger diaphragm diameter. Accordingly, the two diaphragm configuration has an advantage of having a smaller and more compact configuration within the sensor housing 170.

Figure 3A:
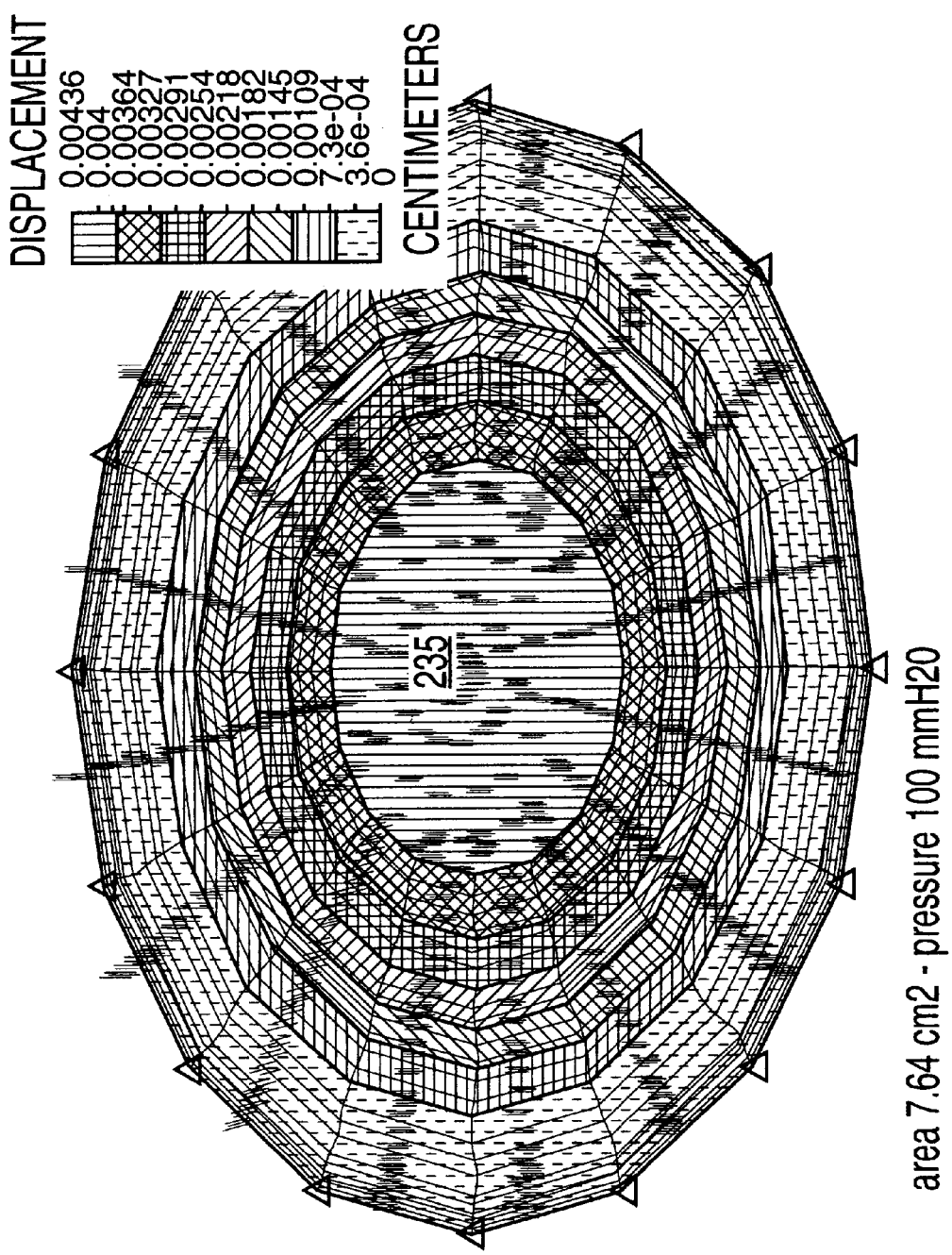
FIG. 3a illustrates a computer simulation of a fluid pressure applied on a conventional diaphragm having flexible parts with approximately circular concentric regions.
Figure 3B:
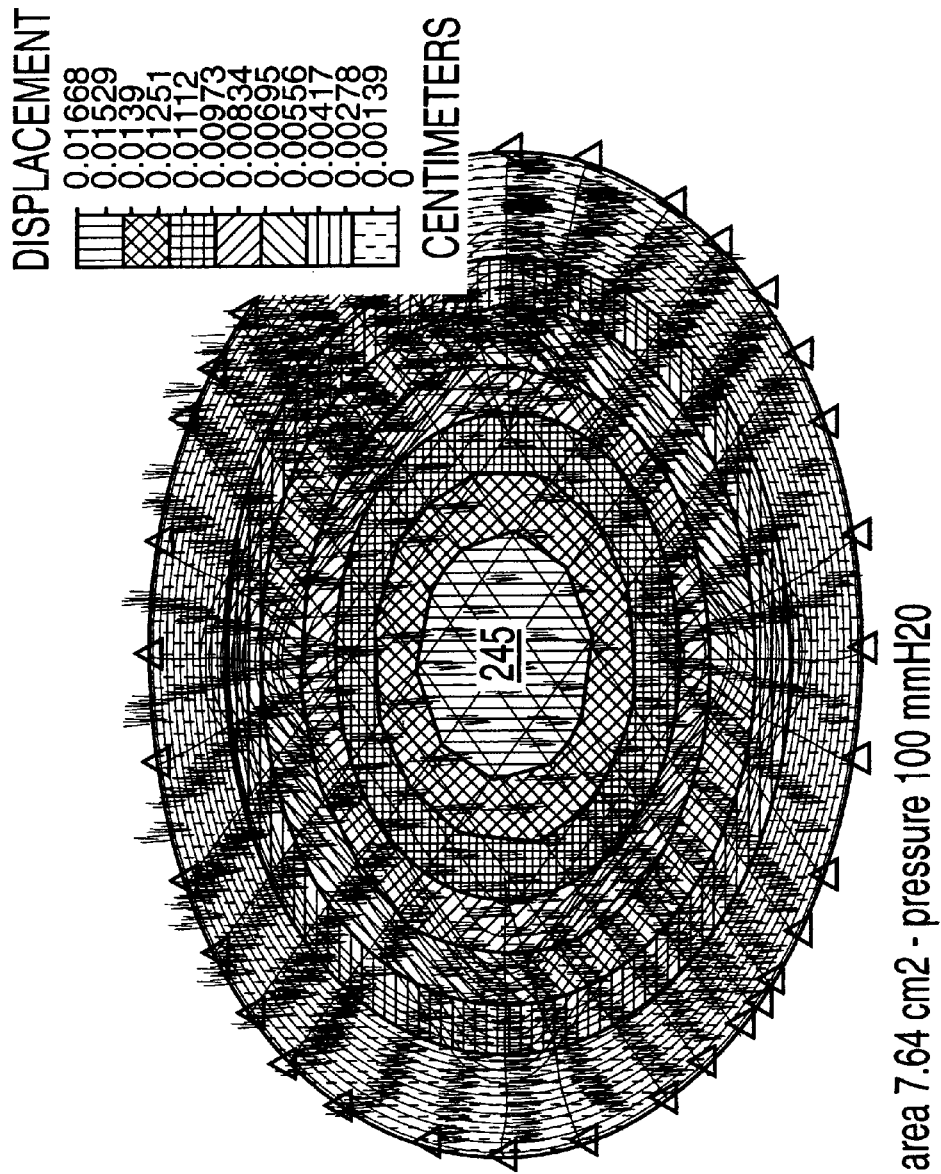
FIG. 3b illustrates a computer simulation of a fluid pressure applied on a diaphragm according to the present invention having flexible parts with the approximately polygonal concentric regions.

FIGS. 3a and 3b illustrate computer simulations of the fluid pressure sensed by the sensors described above. For example, FIG. 3a shows a computer simulation of a center flexible portion 235 of conventional circular concentric region diaphragm which deflects toward a center of a sensor housing for approximately 0.004 centimeters in response to the pressure of 100 millimeters of $H_2O$. FIG. 3b shows a computer simulation of a center flexible portion 245 of a approximately polygonal concentric region diaphragm of the first sensor 80 according to the present invention which deflects toward a center of the sensor housing 170 for approximately 0.01529 centimeters in response to the pressure of 100 millimeters $H_2O$.

In comparison, a displacement of the central flexible portion 235 of the diaphragm of the first sensor 80 according to the present invention (shown in FIG. 3b) was almost four times larger than the central flexible portion of the conventional diaphragm under the same pressure (shown in FIG. 3a). Thus, a use of approximately polygonal concentric flexible portions instead of approximately circular flexible portions may enhance the sensitivity of the diaphragm 180 by approximately four times. Accordingly, the choice of shapes of the flexible parts 220 is a factor to obtain a desired sensitivity for the diaphragm 180.

Figure 4:
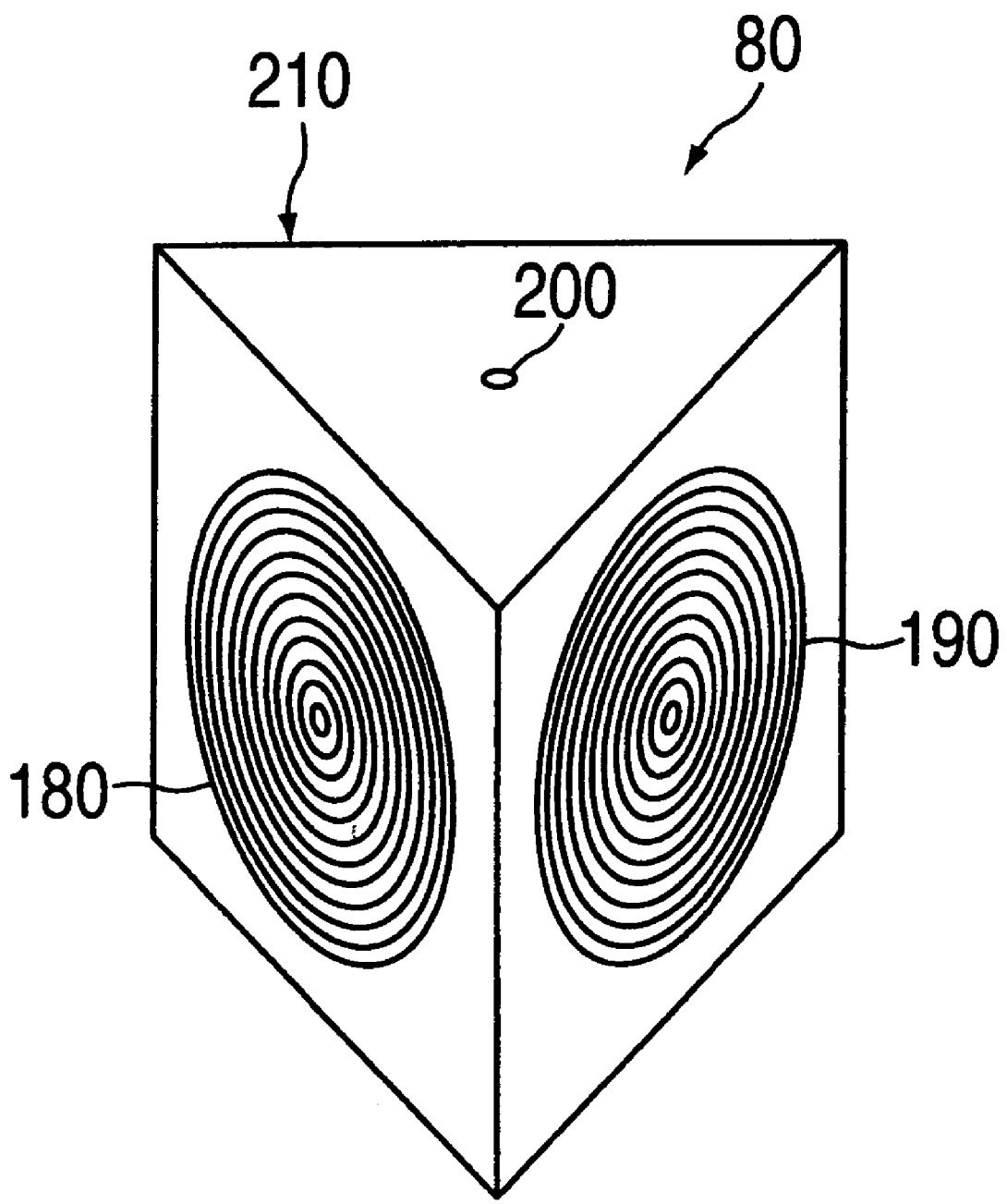

FIG. 4 illustrates another embodiment of the first sensor according to the present invention in which the first sensor 80 has the shape of a triangular prism. With such a shape, three diaphragms 180, 190, 210 may be utilized to measure the fluid pressure. Because this configuration has more diaphragms and thus a greater diaphragm surface area, the diaphragms 180, 190, 210 may have smaller diameters than the diaphragms shown in FIGS. 2a and 2b. The second sensor 100 may have a substantially similar shape as that of the first sensor 80. Similarly, other embodiments may provide sensors having a shape of a cube with four diaphragms. The diaphragms of a sensor in the shape of a cube may be smaller than the diaphragms of the triangular prism shape, and yet provide a similar sensitivity and/or response to the fluid pressure. Other geometric shapes of the sensors are also possible within the scope of the present invention. For example, the first sensor 80 (and/or the second sensor 100) may have a shape of a sphere in which at least one diaphragm covers almost the entire surface area of the sphere, thus achieving even a smaller shape of the first sensor 80.

Figure 5:
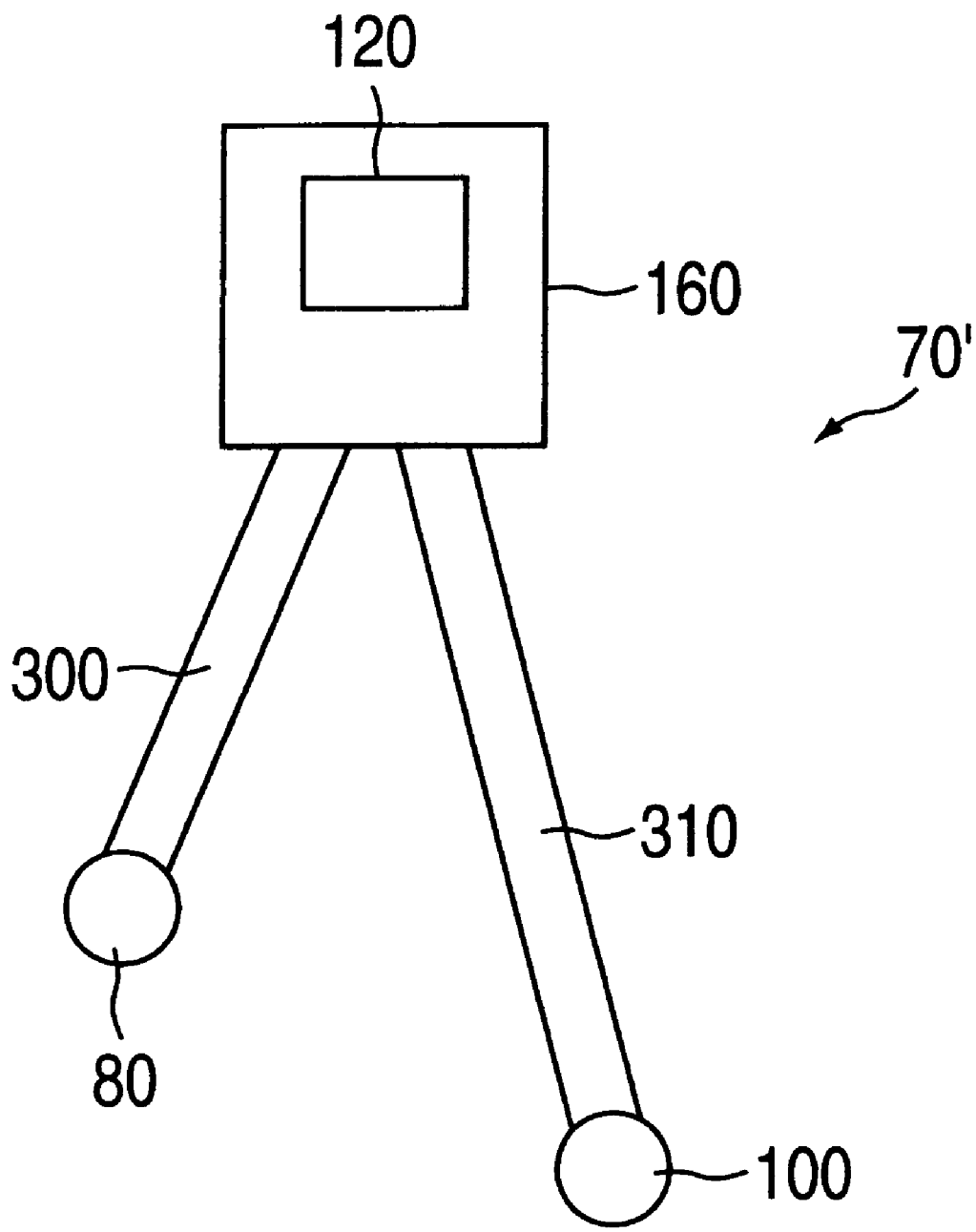
FIG. 5 illustrates another embodiment of the system for measuring fluid density according to the present invention.

FIG. 5 illustrates another embodiment of the present invention. In this embodiment, the first sensor 80 is coupled to the transmitter housing 160 via a first extension 300. The second sensor 100 is coupled to the transmitter housing 160 via a second extension 310. Thus, each of the first and second sensors 80, 100 communicates with the transmitter 120 via a separate fluid path. Accordingly, in this embodiment, the first and second sensors 80, 100 and the transmitter 120 are not co-linear. The operation and use of this device are similar to the operation and use of the embodiments of the system 60 described above.

Although the foregoing invention has been described in terms of certain preferred embodiments, other preferred embodiments will become apparent to those of ordinary skill in the art in view of the disclosure herein. Accordingly, the present invention is not intended to be limited by the recitation of preferred embodiments, but is intended to be defined solely by reference to the appended claims.

What is claimed is:

1. A system for determining a density of a sample fluid in a tank, comprising:
   a sensor fluid housing situated within the tank and containing a first substantially static sensor fluid and a second substantially static sensor fluid, the sensor fluid housing maintaining the first and second sensor fluids separate from the sample fluid;
   a first sensor situated within the tank, the first sensor being coupled to the sensor fluid housing, the first sensor disposed in the tank at a first fluid level of the sample fluid, the first sensor detecting a first fluid pressure at the first fluid level by acting on the first substantially static sensor fluid;
   a second sensor situated within the tank, the second sensor being coupled to the sensor fluid housing, the second sensor disposed in the tank at a second fluid level of the sample fluid, the second sensor detecting a second fluid pressure at the second fluid level by acting on the second substantially static sensor fluid, the second sensor being positioned at a predetermined distance from the first sensor; and
   a transmitter communicating with the first sensor via the first substantially static sensor fluid and communicating with the second sensor via the second substantially static sensor fluid, the transmitter generating at least one signal corresponding to the density of the sample fluid, the at least one signal being generated as a function of the first fluid pressure and the second fluid pressure.

2. The system according to claim 1, further comprising:
   a calculating device coupled to the transmitter, the calculating device calculating the density of the sample fluid in the tank as a function of the at least one signal received from the transmitter.

3. The system according to claim 2, wherein the calculating device is a computer system.

4. The system according to claim 3, wherein the transmitter is coupled to the computer system via a first data bus and a second data bus.

5. The system according to claim 3, wherein the transmitter and the computer system communicate with one another using a wireless communications arrangement.

6. The system according to claim 1, wherein a housing fluid is composed of the first substantially static sensor fluid and the second substantially static sensor fluid.

7. The system according to claim 1, wherein the first substantially static sensor fluid includes at least one of a silicone oil, a fluorolube oil and a propylene glycol oil.

8. The system according to claim 1, wherein the second substantially static sensor fluid includes at least one of a silicone oil, a fluorolube oil and a propylene glycol oil.

9. The system according to claim 1, wherein the first substantially static sensor fluid is at least partially provided in a first tube of the sensor fluid housing, the first tube extending from the first sensor to the transmitter.

10. The system according to claim 1, wherein the second substantially static sensor fluid is at least partially provided in a second tube of the sensor fluid housing, the second tube extending from the first sensor to the transmitter.

11. The system according to claim 1,
wherein the first sensor includes a first sensor housing situated within the tank and a first set of at least two diaphragms coupled to the first sensor housing, and
wherein the second sensor includes a second sensor housing situated within the tank and a second set of at least two diaphragms coupled to the first sensor housing.

12. The system according to claim 11,
wherein the first sensor housing has a cylindrical shape,
wherein the first set includes a first diaphragm and a second diaphragm, and
wherein the first diaphragm is mounted within the first sensor housing at a first edge, and the second diaphragm is mounted within the first sensor housing at a second edge, the first edge being provided opposite to the second edge.

13. The system according to claim 11,
wherein the second sensor housing has a cylindrical shape,
wherein the second set includes a first diaphragm and a second diaphragm, and
wherein the first diaphragm is mounted within the second sensor housing at a first edge, and the second diaphragm is mounted within the second sensor housing at a second edge, the first edge being provided opposite to the second edge.

14. The system according to claim 11, wherein each of the at least two diaphragms of the first set acts on the first substantially static sensor fluid to displace the first substantially static sensor fluid.

15. The system according to claim 11, wherein each of the at least two diaphragms of the second set acts on the second substantially static sensor fluid to displace the second substantially static sensor fluid.

16. The system according to claim 11,
wherein the first sensor housing has a triangular prism shape, and
wherein the first set of at least two diaphragms includes at least three diaphragms, each of the at least three diaphragms being mounted on a separate side of the first sensor housing.

17. The system according to claim 11,
wherein the second sensor housing has a triangular prism shape, and
wherein the second set of at least two diaphragms includes at least three diaphragms, each of the at least three diaphragms being mounted on a separate side of the second sensor housing.

18. The system according to claim 11, wherein each diaphragm in the first and second sets of at least two diaphragms has at least one concentric flexible portion.

19. The system according to claim 1, wherein each of the first and second sensors has an approximately spherical shape and includes a sensor housing and at least one diaphragm substantially covering a surface of the approximately spherical shape.

20. The system according to claim 1, wherein the first sensor and the second sensor are mounted to the sensor fluid housing.

21. The system according to claim 1, wherein the first sensor and the second sensor are integral with the sensor fluid housing.

22. A system for determining a density of a sample fluid in a tank, comprising:
a sensor housing situated within the tank;
a first sensor situated within the tank coupled to the housing via a first extension situated within the tank;
a second sensor situated within the tank coupled to the housing via a second extension situated within the tank, the first sensor positioned at a first fluid level of the sample fluid and sensing a first fluid pressure at the first fluid level by providing a first substantially static sensor fluid via the first extension, the second sensor positioned at a second fluid level of the sample fluid and sensing a second fluid pressure at the second fluid by providing a second substantially static sensor fluid via the second extension, the second fluid level being different from the first fluid level; and
a transmitter provided in the housing, the transmitter being in fluid communication with the first sensor via the first substantially static sensor fluid in the first extension, and being in fluid communication with the second sensor via the second substantially static sensor fluid in the second extension, the transmitter generating at least one signal which relates to the first and second fluid pressures;
wherein the first and second substantially static sensor fluids are maintained separately from the sample fluid by the housing.

23. The system according to claim 22, wherein the first extension and the second extension are aligned along a same longitudinal axis.

24. The system according to claim 22, wherein the first extension and the second extension extend at different longitudinal axes.

25. The system according to claim 22, further comprising:
a calculating device coupled to the transmitter, the calculating device calculating the fluid density of the sample fluid in the tank as a function of the at least one signal received from the transmitter.

26. A sensor for determining a pressure of a sample fluid, comprising:
a sensor housing having a substantially static sensor fluid; and
at least two diaphragms provided in the sensor housing, each of the at least two diaphragms acting on the substantially static sensor fluid in response to the pressure provided by the sample fluid.

27. The sensor according to claim 26, wherein the sensor housing includes a portion for displacing the substantially static sensor fluid in the sensor when the at least two diaphragms act on the substantially static sensor fluid.

28. The sensor according to claim 26,
wherein the sensor housing has a cylindrical shape, and
wherein the at least two diaphragms include a first and a second diaphragm, the first diaphragm being mounted within the sensor housing at a first edge, the second diaphragm being mounted at a second edge, the first edge being opposite to the second edge.

29. The sensor according to claim 26,
wherein the sensor housing has a triangular prism shape, and wherein the at least two diaphragms include at least three diaphragms, each of the three diaphragms being mounted on a separate side of the sensor housing.

30. The sensor according to claim 26, wherein each of the at least two diaphragms has at least one concentric flexible portion.

31. The sensor according to claim 30, wherein each of the at least one concentric flexible portions has at least one of a circular shape and a polygonal shape.

32. The sensor according to claim 26, wherein the sensor housing has an approximately spherical shape.

33. The sensor according to claim 26, wherein the sensor is composed of at least one of a stainless steel material, a hastelloy material, a Monel material, a tantalum material and a titanium material.

34. A sensor for determining a pressure of a sample fluid, comprising:
   a sensor housing having an approximately spherical shape, the sensor housing enclosing a substantially static sensor fluid; and
   at least one diaphragm coupled to the sensor housing, the at least one diaphragm acting on the substantially static sensor fluid in response to the pressure provided by the sample fluid.

35. A method for determining a density of a sample fluid in a tank, comprising the steps of:
   providing a first sensor situated within the tank at a first fluid level in the sample fluid;
   providing a second sensor situated within the tank at a second fluid level in the sample fluid, the second fluid level being different from the first fluid level;
   sensing a first fluid pressure of the sample fluid at the first fluid level using the first sensor to act on a first substantially static sensor fluid, the first substantially static sensor fluid being maintained separately from the sample fluid, and the first sensor communicating with a transmitter using the first substantially static sensor fluid;
   sensing a second fluid pressure of the sample fluid at the second fluid level using a second sensor to act on a second substantially static sensor fluid, the second substantially static sensor fluid being maintained separately from the sample fluid, and the second sensor communicating with the transmitter through the second substantially static sensor fluid; and
   generating at least one signal relating to the first fluid pressure and the second fluid pressure to determine the density of the particular fluid.

36. The method according to claim 35, further comprising the step of:
   determining the density of the particular fluid in the tank as a function of the at least one signal.

37. The method according to claim 35, wherein the step of sensing the first fluid pressure includes the substep of applying the first fluid pressure to at least two diaphrams which are coupled to the first sensor, the at least two diaphragms bending to displace the first substantially static sensor fluid in the first sensor.

38. The method according to claim 35, wherein the step of sensing the second fluid pressure includes the substep of applying the second fluid pressure to at least two diaphragms which are coupled to the second sensor, the at least two diaphragms bending to displace the second substantially static sensor fluid in the second sensor.

39. The method according to claim 35, wherein the first and second sensors are maintained at a predetermined distance from one another by coupling the first sensor to a first end of an extension member and the second sensor to a second end of the extension member.

40. A method for measuring a fluid pressure of a sample fluid, comprising the steps of:
   providing a sensor situated within the sample fluid at a fluid level, the sensor including a sensor housing, at least two diaphragms and a substantially static sensor fluid, the at least two diaphragms being coupled to the sensor housing, the at least two diaphragms being affected by the fluid pressure of the fluid level, the at least two diaphragms acting on the substantially static sensor fluid; and
   determining the fluid pressure of the fluid at the fluid level by measuring the fluid pressure of the substantially static sensor fluid;
   wherein the substantially static sensor fluid and the sample fluid are maintained separately from one another.

41. A sensor for determining a pressure of a sample fluid, comprising:
   a sensor housing containing a substantially static sensor fluid; and
   at least one diaphragm disposed in the sensor housing and acting on the substantially static sensor fluid in response to the pressure provided by the sample fluid,
   wherein the substantially static sensor fluid and the sample fluid are maintained separately from one another and the at least one diaphragm includes a concentric flexible portion having a non-circular shape.

42. The sensor according to claim 41, wherein the concentric flexible portion has a polygonal shape.

43. The sensor according to claim 41, wherein the concentric flexible portion has a substantially rectangular shape.

44. The sensor according to claim 41, wherein the concentric flexible portion has an indentation portion which extends in a non-circular manner along an edge of the at least one diaghram.

* * * * *